(12) United States Patent
Petty

(10) Patent No.: US 7,682,834 B1
(45) Date of Patent: Mar. 23, 2010

(54) COLORIMETRIC TEST FOR BRAKE FLUID

(76) Inventor: Jon A. Petty, P.O. Box 559, Loa, UT (US) 84747

( * ) Notice: Subject to any disclaimer, the term of this patent is extended or adjusted under 35 U.S.C. 154(b) by 0 days.

(21) Appl. No.: 12/263,987

(22) Filed: Nov. 3, 2008

(51) Int. Cl.
*G01N 21/78* (2006.01)
*G01N 21/77* (2006.01)

(52) U.S. Cl. .................. 436/169; 436/164; 436/166; 422/55; 422/56; 73/39; 73/121

(58) Field of Classification Search ............ 436/164, 436/166, 169; 422/55, 56, 61; 73/39, 53.01, 73/121
See application file for complete search history.

(56) References Cited

U.S. PATENT DOCUMENTS

| | | | | |
|---|---|---|---|---|
| 5,856,199 A | * | 1/1999 | Kreiser et al. | 436/169 |
| 6,043,096 A | * | 3/2000 | Evtodienko et al. | 436/39 |
| 6,651,487 B1 | * | 11/2003 | Petty | 73/61.46 |
| 6,691,562 B2 | * | 2/2004 | Petty | 73/61.46 |
| 6,821,786 B2 | * | 11/2004 | Rupp | 436/73 |
| 2008/0206874 A1 | * | 8/2008 | Manka | 436/2 |

FOREIGN PATENT DOCUMENTS

WO 01/06225 * 1/2001

* cited by examiner

*Primary Examiner*—Maureen M Wallenhorst
(74) *Attorney, Agent, or Firm*—Quarles & Brady LLP; Gavin J. Milczarek-Desai

(57) ABSTRACT

A method for determining a type of brake fluid that includes contacting a colorimetric reagent on a substrate. An embodiment of the method reacts to the presence of a borate ester in brake fluid to produce a color contacted by DOT 4/5.1 brake fluid or a second color in the presence of pure DOT 3 fluid. In the event of mixtures of DOT 3 with DOT 4/5.1, a third color results when contacted by a mixture of DOT 3 and DOT 4/5.1 brake fluid in which the DOT 4/5.1 fluid is about 50% or less of the mixture.

11 Claims, 3 Drawing Sheets

ALBANY™
BRAKE FLUID
DOT 3

PRESTONE™
BRAKE FLUID
DOT 3

PRESTONE™
BRAKE FLUID
DOT 4

VALVOLINE™
SynPOWER™
BRAKE FLUID
DOT 3 & DOT 4

ATE
BREMSFLÜSSIGKEIT SL™
DOT 4

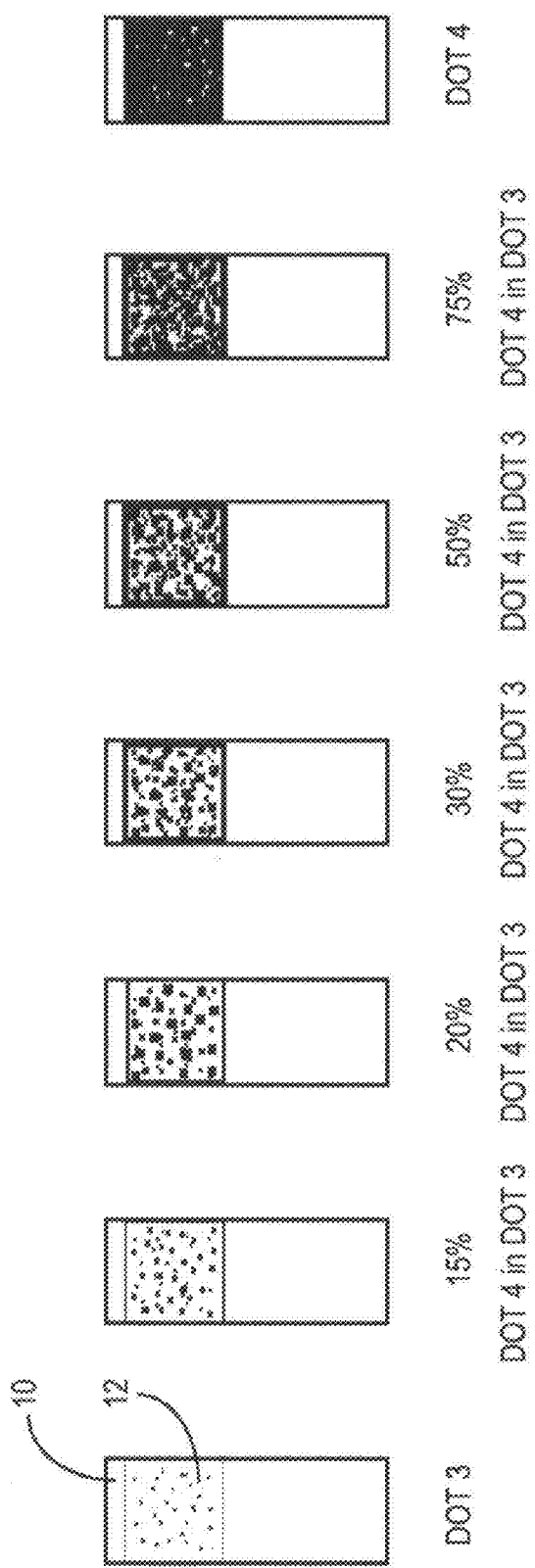

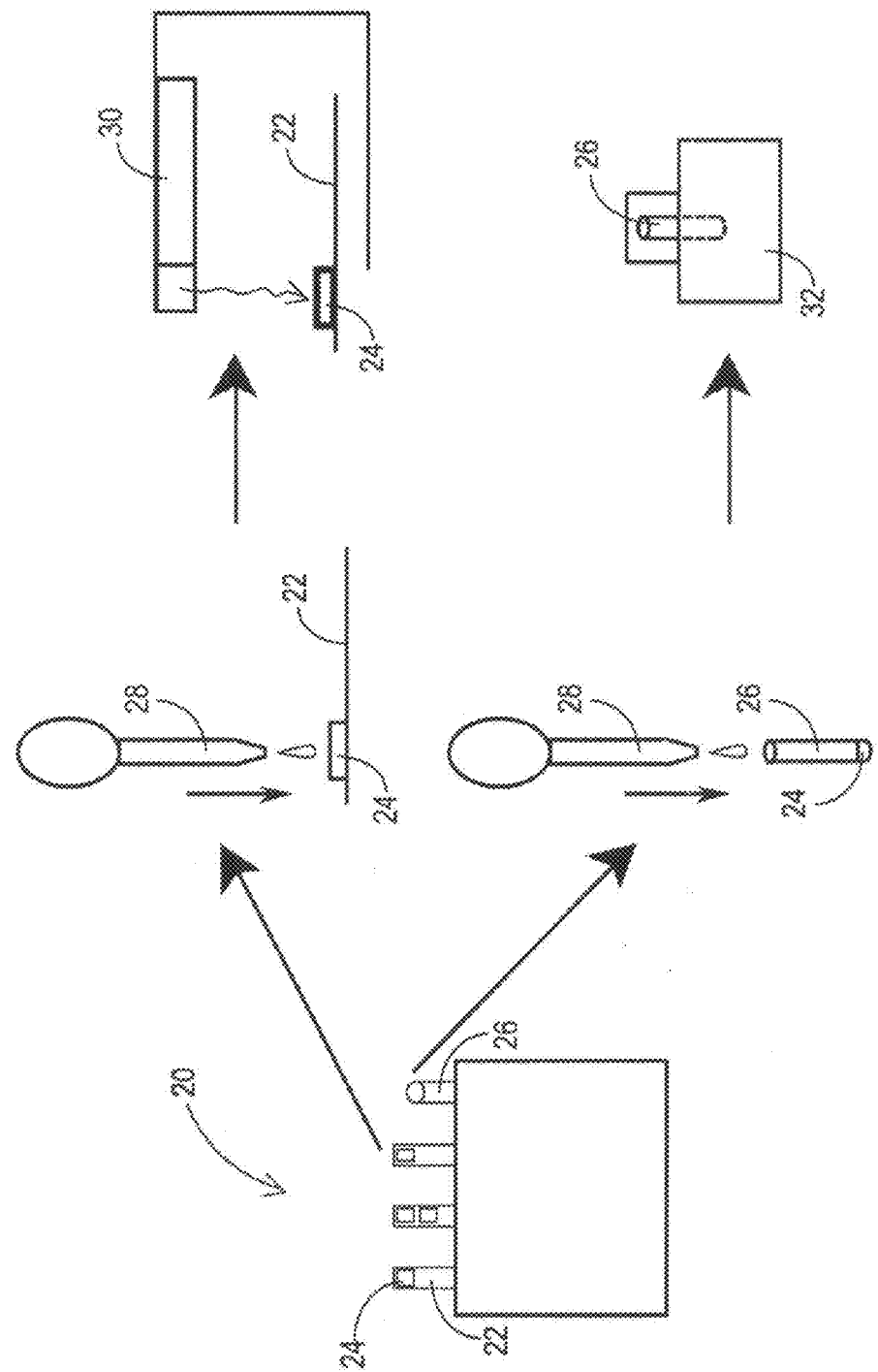

COLORIMETRIC TEST FOR BRAKE FLUID

BACKGROUND OF THE INVENTION

Description of the Related Art

Brake fluid tests have been in use for years to identify corrosion and to detect other problems with brake fluid. Conventional on-site (e.g., at a service or inspection station) brake fluid tests currently used are copper brake fluid test strips, moisture test strips and boiling point analyzers. The main problem with conventional brake fluid tests are that they can not determine the type of brake fluid in the vehicle brake system.

Another problem with convention brake fluid test are that they can not be used by an automotive service facility that complies with the Motorist Assurance Program (MAP) guidelines for brake fluid replacement. Part of the MAP guidelines require that brake fluid be replaced if it is the incorrect type. For example, a vehicle where the original equipment manufacturer has specified that the brake system must use "DOT 4 brake fluid only." This designation is found in on the master cylinder reservoir lid or cap. If this vehicle is found to contain DOT 3 brake fluid, the brake fluid must be replaced because DOT3 brake fluid has a lower wet and dry boiling point and other lower performance criteria. There is no current available technology that can easily identify this common problem in a short amount of time. Therefore, these current on-site methods are of no value in identifying whether the fluid needs to be replaced to meet the original equipment manufacturer (OEM) specification.

Conventional off-site brake fluid testing methods can be expensive. In addition, the amount of time to test and analyze the results of a conventional off-site brake fluid testing method can be a lengthy process, requiring at least two weeks time before the results can be returned. For example, to accurately determine the type of brake fluid in a vehicle brake system, a sample of brake fluid must be sent to a testing laboratory. This type of laboratory testing is not practical for a service facility to use during regular vehicle inspection procedures. Currently, there is no visual test to identify DOT 3 and DOT 4 or DOT 5.1 brake fluid without having to withdraw a sample of the brake fluid and send it to a laboratory for analysis.

SUMMARY OF THE INVENTION

The invention primarily relates to a method, apparatus and test kit for visually determining a type of brake fluid quickly and in a cost-efficient manner. Another objective of this invention is determining if there is a minority of DOT 4 mixed with a majority of DOT 3 in a brake system.

In its preferred embodiment, the invention comprises a colorimetric reagent that results in a first color when contacted by DOT 3 brake fluid, a second color when contacted by DOT 4 and/or 5.1 brake fluid, and a third color when contacted by a mixture of DOT 3 and DOT 4 and/or 5.1 brake fluid when the DOT 4 and/or DOT 5.1 represent about 50% or less of the DOT 3 and DOT 4/5.1 mixture.

DOT 3 fluid is an aliphatic polyether, whereas DOT 4 and DOT 5.1 are borate ester based. Thus, an embodiment of the invention may be described as a method of distinguishing a borate ester based brake fluid from a brake fluid that lacks borate esters. Another embodiment may be described as method of detecting the presence of a borate ester based brake fluid in a mixture of brake fluids (e.g., detecting whether DOT 4 and/or DOT 5.1 fluid has been mixed with or substituted for DOT 3 fluid in a vehicle requiring same.

In one embodiment, the third color may vary with the concentration of DOT 4/5.1 brake fluid up to about a 50% concentration of such fluid mixed with another. After the DOT 4/5.1 fluid exceeds 50%, the color is substantially the same as for 100% of a DOT 4/5.1 fluid.

In another embodiment, the present invention utilizes a substrate, such as a dipstick, or a kit with a visual color chart that provides an easy color comparison for determining the results of the test. An automated embodiment of the invention includes an electronic color detector to automatically determine the results of the test by inserting the colorimetric reagent into the electronic color tester after making contact with the brake fluid to automatically determine the presence of DOT 3 or DOT 4/5.1 brake fluid and/or a mixture of DOT 3 and DOT 4/5.1 within the brake system.

BRIEF DESCRIPTION OF THE DRAWINGS

The invention will be better understood from a reading of the following detailed description taken in conjunction with the drawings in which like reference designators are used to designate like elements, and in which:

FIG. 2 is brake fluid color test demonstrating a varying color for certain mixtures of DOT 3 and DOT 4 brake fluid.

FIG. 3 is a schematic illustration of a kit embodiment of the invention.

DETAILED DESCRIPTION OF THE PREFERRED EMBODIMENTS

This invention is described in preferred embodiments in the following description with reference to the Figures, in which like numbers represent the same or similar elements.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
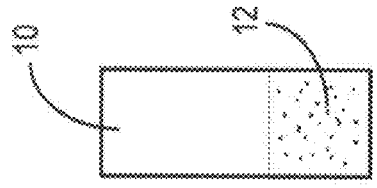
FIG. 1 is brake fluid color tests for DOT 3 and DOT 4 brake fluids according to the invention.
Figure 1:
Figure 1:
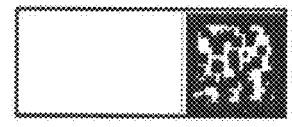
Figure 1:
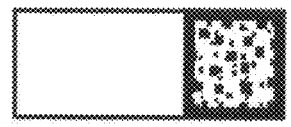
Figure 1:
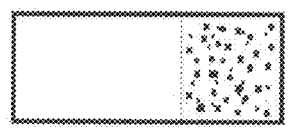

Applicant's invention comprises a colorimetric reagent that, when contacted with a brake fluid, results in a first color if contacted by DOT 3 brake fluid or a second color if contacted by DOT 4/5.1 brake fluid. The reagent further may become a third color when contacted by a mixture of DOT 3 and DOT 4/5.1 brake fluid. Referring now to FIG. 1, the colorimetric reagent or equivalents thereof must be reactive to a borate ester contained in certain brake fluids (e.g., DOT 4 and 5.1, which are referred to as DOT 4/5.1 for simplicity). Preferably, the colorimetric reagent changes color when contacted by borate ester-containing brake fluid in a pronounced way, such as from yellow to red.

The colorimetric reagent reacts with borate ester containing brake fluids (e.g., DOT 4/5.1), causing a color reaction. The regent may be substantially non-reactive with brake fluids the do not contain a borate ester (e.g., DOT 3 fluid), thereby remaining a starting color. If a borate ester containing brake fluid is mixed with one or more fluid that do not contain a borate ester, a third color results according to the concentration of the borate ester containing brake fluid, up to about a 50% concentration of the borate ester containing fluid.

In certain embodiments, a yellow color results when the colorimetric reagent is exposed to DOT3 brake fluid or a red color with exposure to DOT 4/5.1 brake fluids. If a mixture of up to 50% DOT 4/5.1 and DOT 3 is present, an orange color that varies with the concentration of DOT 4/5.1 develops. In certain embodiments, the colorimetric reagent color change can be determined with the use of a color chart or scale for reference purposes. In one embodiment, the colorimetric reagent remains a liquid in a container, such as a tube, wherein a sample of brake fluid is added. In one embodiment, it is also possible to use an electronic color tester (such as a spectra-photometer) to read the color reaction for automated determination of results, which can be assistive for those otherwise visually impaired or incapable of determining the color reaction (or small reactions).

Referring to FIG. 1, a dip test strips 10 having colormetric reagent 12 disposed thereon are dipped into a sample of brake fluid for one second. The colormetric reagent may be any known to react with a borate ester to produce a color change. After shaking off excess fluid and waiting approximately 3 minutes, the strips dipped in DOT 3 fluid show a yellow coloration, while those dipped in DOT 4 show a red coloration. One sample of a mixture of DOT 4 with DOT 3 fluid results in a red coloration, indicating that the DOT 4 fluid is at least about 50% of the content.

Referring now to FIG. 2, a dip test strips 10 having colormetric reagent 12 disposed thereon are dipped into a sample of brake fluid for one second. After shaking off excess fluid and waiting approximately 3 minutes, the strip dipped in DOT 3 fluid shows a yellow coloration, while that dipped in DOT 4 shows a red coloration. Up to about a 50% concentration of DOT 4 in a DOT 4/DOT 3 fluid mixture, test strips 10 display an orange color that varies in intensity according to the DOT 4 concentration. After about 50% or more of DOT 4, the color becomes red as with pure DOT 4.

As shown in FIG. 3, a kit 20 of the invention includes a plurality of substrates (e.g., strips 22 and/or tubes 26) upon or within which colorimetric reagent 24 is disposed. A small sample of brake fluid 28 is dispensed from a dropper onto strip 22 or within tube 26, which may have the colorimetric reagent 24 already disposed within or added separately. Thus, brake fluid sample 28 contacts the colorimetric reagent and may be read manually for color content or with the aid of color testing machines. For example, a strip reading spectrophotometer 30 or tube reading spectrophotometer 32 may be employed to read the resulting color and provide a reading that correlates with the presence of a borate ester containing brake fluid. Of course, the colorimetric reagent may be disposed upon or within materials that are rigid, flexible and of various styles, shapes and sizes.

While the preferred embodiments of the present invention have been illustrated in detail, it should be apparent that modifications and adaptations to those embodiments may occur to one skilled in the art without departing from the scope of the present invention.

What is claimed is:

1. A method for determining a Department of Transportation (DOT) type of brake fluid, comprising the steps of:
    (a) providing a colorimetric reagent and a brake fluid sample;
    (b) contacting said colorimetric reagent with said brake fluid sample, wherein said colorimetric reagent results in a first color when contacted by DOT 3 brake fluid or a second color when contacted by a DOT 4/5.1 brake fluid; and
    (c) determining that the brake fluid sample is DOT 3 by observing said first color or is DOT 4/5.1 by observing said second color.

2. The method of claim 1, wherein said reagent further results in a third color when contacted by a mixture of DOT3 and DOT 4/5.1 brake fluid and wherein the DOT 4/5.1 brake fluid comprises no more than about 50% of said mixture.

3. The method of claim 2, wherein said third color varies with the concentration of DOT 4/5.1 brake fluid up to about a 50% concentration of said brake DOT 4/5.1 brake fluid in said mixture.

4. The method of claim 1, wherein said colorimetric reagent is reactive to a borate ester.

5. The method of claim 1, wherein said colorimetric reagent is affixed to a strip or dipstick.

6. The method of claim 1, wherein step (c) comprises analyzing said colorimetric reagent in an electronic color tester.

7. A method for determining a type of brake fluid, comprising the steps of:
    (a) providing a colorimetric reagent and sample of brake fluid;
    (b) contacting said colorimetric reagent with said brake fluid sample, wherein said colorimetric reagent results in a first color when contacted by a brake fluid that does not contain a borate ester or a second color when contacted by a brake fluid that does contain a borate ester;
    (c) determining that the brake fluid sample does not contain said borate ester by observing said first color or does contain said borate ester by observing said second color.

8. The method of claim 7, wherein said reagent further results in a third color when contacted by a mixture of borate ester and non-borate ester containing brake fluids and wherein the borate ester containing brake fluid comprises no more than about 50% of said mixture.

9. The method of claim 8, wherein said third color varies with the concentration of borate ester containing brake fluid up to about a 50% concentration of said borate ester containing brake fluid in said mixture.

10. The method of claim 7, wherein said colorimetric reagent is affixed to a strip or dipstick.

11. The method of claim 7, wherein step (c) comprises analyzing said colorimetric reagent in an electronic color tester.

* * * * *